United States Patent
Lu et al.

(10) Patent No.: US 11,885,865 B2
(45) Date of Patent: Jan. 30, 2024

(54) QUALITY CONTROL PHANTOM AND EVALUATION METHOD FOR MAGNETIC RESONANCE ARTERIAL SPIN LABELING PERFUSION IMAGING

(71) Applicant: SHANDONG FIRST MEDICAL UNIVERSITY & SHANDONG ACADEMY OF MEDICAL SCIENCES, Shandong (CN)

(72) Inventors: Weizhao Lu, Tai'an (CN); Kun Hou, Tai'an (CN); Jianfeng Qiu, Tai'an (CN); Liting Shi, Tai'an (CN); Huihui Zhao, Tai'an (CN)

(73) Assignee: SHANDONG FIRST MEDICAL UNIVERSITY & SHANDONG ACADEMY OF MEDICAL SCIENCES, Tai'an (CN)

( * ) Notice: Subject to any disclaimer, the term of this patent is extended or adjusted under 35 U.S.C. 154(b) by 309 days.

(21) Appl. No.: 17/427,996

(22) PCT Filed: Nov. 25, 2019

(86) PCT No.: PCT/CN2019/120740
§ 371 (c)(1),
(2) Date: Aug. 3, 2021

(87) PCT Pub. No.: WO2020/164292
PCT Pub. Date: Aug. 20, 2020

(65) Prior Publication Data
US 2022/0120836 A1 Apr. 21, 2022

(30) Foreign Application Priority Data
Feb. 12, 2019 (CN) .......................... 201910111798.X

(51) Int. Cl.
*G01R 33/56* (2006.01)
*G01R 33/563* (2006.01)
*A61B 5/026* (2006.01)

(52) U.S. Cl.
CPC ...... *G01R 33/56366* (2013.01); *A61B 5/0263* (2013.01)

(58) Field of Classification Search
CPC .............. G01R 33/56366; G01R 33/58; A61B 5/0263; A61B 2560/0228; A61B 5/055
See application file for complete search history.

(56) References Cited

U.S. PATENT DOCUMENTS

| | | | | |
|---|---|---|---|---|
| 2009/0316972 | A1* | 12/2009 | Borenstein | A61B 6/583 378/207 |
| 2011/0293074 | A1* | 12/2011 | Coolens | G09B 23/303 378/207 |
| 2019/0033419 | A1 | 1/2019 | Golay et al. | |

FOREIGN PATENT DOCUMENTS

| | | |
|---|---|---|
| CN | 101329388 A | 12/2008 |
| CN | 103430211 A | 12/2013 |

(Continued)

OTHER PUBLICATIONS

Feb. 27, 2020 International Search Report issued in International patent Application No. PCT/CN2019/120740.

(Continued)

*Primary Examiner* — G. M. A Hyder
(74) *Attorney, Agent, or Firm* — Oliff PLC

(57) ABSTRACT

A quality control phantom and an evaluation method for magnetic resonance arterial spin labeling perfusion imaging includes: a phantom main body; a container, a circulating liquid being provided in the container; a tube, comprising a first tube and a second tube, one end of the first tube being in communication with the container, the other end being in communication with a liquid inlet of the phantom main (Continued)

body, one end of the second tube being in communication with the container, the other end being in communication with a liquid outlet of the phantom main body, and the first tube, the phantom main body, the second tube and the container jointly forming a closed loop; a pump, provided on the first tube and used to drive the circulating liquid to circulate along the closed loop to generate a perfusion signal in the phantom main body.

4 Claims, 2 Drawing Sheets

(56) References Cited

FOREIGN PATENT DOCUMENTS

| CN | 106377261 A | 2/2017 |
|---|---|---|
| CN | 107851401 A | 3/2018 |
| CN | 109669151 A | 4/2019 |
| CN | 209656869 U | 11/2019 |

OTHER PUBLICATIONS

Feb. 27, 2020 Written Opinion issued in International patent Application No. PCT/CN2019/120740.

* cited by examiner

QUALITY CONTROL PHANTOM AND EVALUATION METHOD FOR MAGNETIC RESONANCE ARTERIAL SPIN LABELING PERFUSION IMAGING

BACKGROUND

Technical Field

The present disclosure belongs to the field of phantom design, and in particular relates to a quality control phantom and an evaluation method for magnetic resonance arterial spin labeling perfusion imaging.

Related Art

The description in this section merely provides background information related to the present disclosure and does not necessarily constitute the prior art.

Changes of cerebral blood flow (CBF) will occur in common encephalomyopathies such as cerebrovascular diseases, tumors and epilepsy, so it is of great value to measure the CBF of brain in clinic. Magnetic resonance Arterial Spin Labeling (ASL) technology is a magnetic resonance imaging technology that quantitatively measures the blood perfusion of brain tissues by using magnetic labeling of arterial blood as an endogenous contrast agent.

At present, ASL technology has been widely used in magnetic resonance imaging systems of major manufacturers. Major manufacturers and researchers have carried out a lot of verification work for ASL perfusion measurement, including clinical feasibility study in animals and humans, comparative tests with PET and other perfusion technologies, and repeatability tests, which have proved the accuracy of ASL perfusion imaging. However, as found by the inventor, there is still a lack of a tool for quantitative verification and evaluation of ASL perfusion imaging.

SUMMARY

In order to solve the problem, a first aspect of the present disclosure provides a quality control phantom for magnetic resonance arterial spin labeling perfusion imaging, which can quantitatively verify and evaluate the accuracy of magnetic resonance ASL perfusion imaging.

The quality control phantom for magnetic resonance arterial spin labeling perfusion imaging provided by the first aspect of the present disclosure adopts the following technical solution:

The quality control phantom for magnetic resonance arterial spin labeling perfusion imaging provided by the present disclosure includes:
  a phantom main body;
  a container, a circulating liquid being provided in the container;
  a tube, including a first tube and a second tube, one end of the first tube being in communication with the container, the other end being in communication with a liquid inlet of the phantom main body, one end of the second tube being in communication with the container, the other end being in communication with a liquid outlet of the phantom main body, and the first tube, the phantom main body, the second tube and the container jointly forming a closed loop;
  a pump, provided on the first tube and used to drive the circulating liquid to circulate along the closed loop to generate a perfusion signal in the phantom main body.

Further, the phantom main body includes a phantom housing, and a filler is provided in the phantom housing.

The phantom housing may be in any regular geometrical shape such as cylindrical shape and cubic shape, or may be made into an irregular shape equivalent to the brain shape by 3D printing and other technologies.

The filler may be any solid organic substance or gel, such as ABS plastic bead, silica gel, and agarose gel. The purpose of the filler is to fix a hose in the phantom and prevent the hose from winding, refluxing and streaming.

Further, if the shape of the phantom housing is irregular, the phantom housing is also connected with a supporting member.

If the phantom housing is in an irregular shape, a corresponding supporting member is needed to support the phantom main body during magnetic resonance ASL sequence scanning, so as to keep the main body stable during magnetic resonance scanning.

Further, the circulating liquid is a liquid containing hydrogen protons at any normal temperature.

The liquid containing hydrogen protons includes water, aqueous solution, liquid organic matters, etc.

Further, the pump is a controllable flow pump.

The flow of the controllable flow pump can be adjusted manually or mechanically.

Further, the tube is a plastic hose.

The tube is used to connect the circulating liquid and the pump such that the circulating liquid circulates in the phantom main body to generate the perfusion signal. For example, the hose is an ABS plastic hose.

In order to solve the problem, a second aspect of the present disclosure provides a quantitative evaluation method for magnetic resonance arterial spin labeling perfusion imaging, which can quantitatively evaluate and verify magnetic resonance arterial spin labeling perfusion imaging by adopting the quality control phantom for magnetic resonance arterial spin labeling perfusion imaging.

The quantitative evaluation method for magnetic resonance arterial spin labeling perfusion imaging provided by the second aspect of the present disclosure adopts the following technical solution:

The quantitative evaluation method for magnetic resonance arterial spin labeling perfusion imaging provided by the present disclosure includes:
  performing magnetic resonance arterial spin labeling sequence scanning on the quality control phantom for magnetic resonance arterial spin labeling perfusion imaging in a working state by using a magnetic resonance system;
  recording parameters of a magnetic resonance arterial spin labeling sequence, and obtaining a control image and a label image of the phantom after scanning;
  calculating a cerebral blood flow through the control image and the label image;
  performing verification by comparing the calculated cerebral blood flow with an actual flow value of a controllable flow pump.

Further, the method also includes:
  adjusting the flow of the pump and performing repetitive scanning experiments.

The solution has the advantage that the accuracy of quantitative verification of magnetic resonance ASL perfusion imaging can be improved.

Further, the method also includes:
  calculating an average percentage error of cerebral blood flows obtained in repetitive scanning and a correlation coefficient between cerebral blood flows and actual flows.

Further, the smaller the average percentage error of cerebral blood flows is, the closer the correlation coefficient between cerebral blood flows and actual flows is to 1, indicating that the measurement accuracy of magnetic resonance arterial spin labeling cerebral blood flows is higher.

Beneficial effects of the present disclosure are as follows:
(1) The quality control phantom for magnetic resonance arterial spin labeling perfusion imaging provided by the present disclosure includes a phantom main body, a container, a tube and a pump, the tube includes a first tube and a second tube, and the first tube, the phantom main body, the second tube and the container jointly form a closed loop; the pump drives the circulating liquid to circulate along the closed loop to generate a perfusion signal in the phantom main body. The structure is simple, and the accuracy of magnetic resonance ASL perfusion imaging can be quantitatively verified and evaluated.
(2) In the present disclosure, magnetic resonance arterial spin labeling sequence scanning is performed on the quality control phantom for magnetic resonance arterial spin labeling perfusion imaging in a working state by using a magnetic resonance system, and an average percentage error of cerebral blood flows obtained in repetitive scanning and a correlation coefficient between cerebral blood flows and actual flows are calculated. The smaller the average percentage error of cerebral blood flows is, the closer the correlation coefficient between cerebral blood flows and actual flows is to 1, indicating that the measurement accuracy of magnetic resonance arterial spin labeling cerebral blood flows is higher, thus realizing the quantitative evaluation of magnetic resonance arterial spin labeling perfusion imaging.

BRIEF DESCRIPTION OF THE DRAWINGS

The accompanying drawings constituting a part of the present disclosure are used to provide further understanding of the present disclosure. Exemplary embodiments of the present disclosure and descriptions thereof are used to explain the present disclosure, and do not constitute an improper limitation to the present disclosure.

Figure 1:
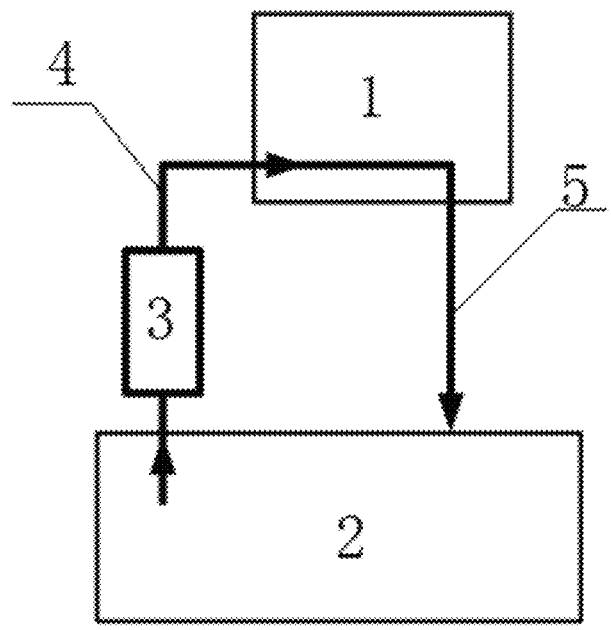
FIG. 1 illustrates a schematic structural diagram of a quality control phantom for magnetic resonance arterial spin labeling perfusion imaging provided by one embodiment of the present disclosure.

In the drawings, 1: phantom main body; 2: container; 3: pump; 4: first tube; 5: second tube; 1-1: phantom housing; 1-2: filler; 1-3: supporting member.

DETAILED DESCRIPTION

It should be noted that the following detailed descriptions are all exemplary and are intended to provide a further description of the present disclosure. Unless otherwise specified, all technical and scientific terms used herein have the same meaning as commonly understood by a person of ordinary skill in the technical field to which the present disclosure belongs.

It should be noted that terms used herein are only for describing specific implementations and are not intended to limit exemplary implementations according to the present disclosure. As used herein, the singular form is also intended to include the plural form unless the context clearly dictates otherwise. In addition, it should further be understood that, terms "include" and/or "include" used in this specification indicate that there are features, steps, operations, devices, components, and/or combinations thereof.

FIG. 1 illustrates a schematic structural diagram of a quality control phantom for magnetic resonance arterial spin labeling perfusion imaging provided by one embodiment of the present disclosure.

Referring to FIG. 1, the quality control phantom for magnetic resonance arterial spin labeling perfusion imaging provided by this embodiment includes:

(1) A phantom main body 1.

Figure 2:
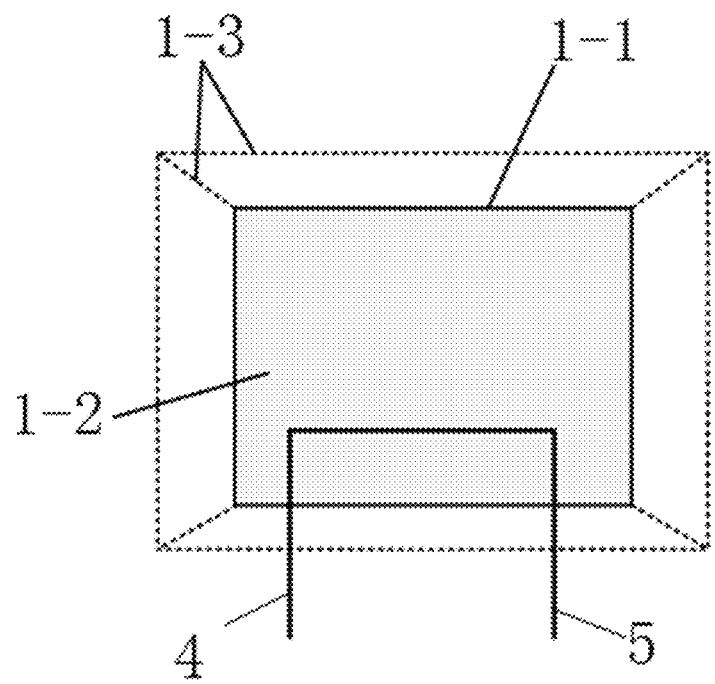
FIG. 2 illustrates a schematic structural diagram of a phantom main body provided by one embodiment of the present disclosure.

Referring to FIG. 2, the phantom main body 1 includes a phantom housing 1-1 and a filler 1-2 is provided in the phantom housing 1-1.

Figure 3:
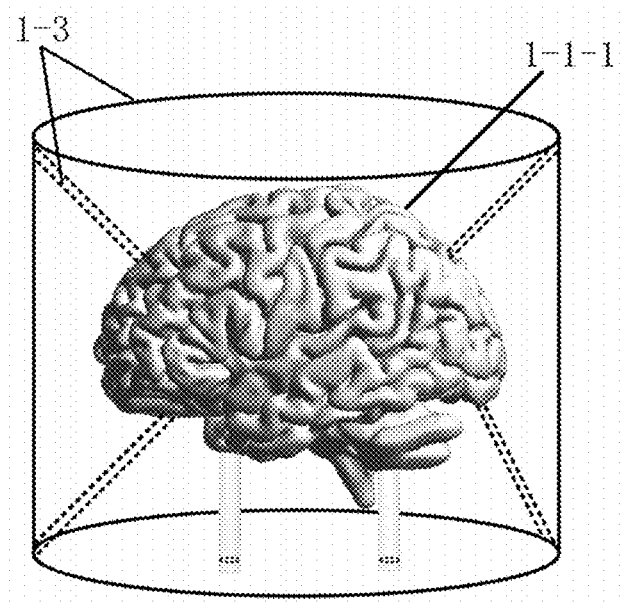
FIG. 3 illustrates a schematic structural diagram of a brain phantom main body provided by one embodiment of the present disclosure.

The phantom housing 1-1 may be in any regular geometrical shape such as cylindrical shape and cubic shape, or, as shown in FIG. 3, may be made into an irregular shape 1-1-1 equivalent to the brain shape by 3D printing and other technologies.

The filler may be any solid organic substance or gel, such as ABS plastic bead, silica gel, and agarose gel. The purpose of the filler is to fix a hose in the phantom and prevent the hose from winding, refluxing and streaming.

If the shape of the phantom housing is irregular, the phantom housing 1-1 is also connected with a supporting member 1-3.

If the phantom housing is in an irregular shape, a corresponding supporting member is needed to support the phantom main body during magnetic resonance ASL sequence scanning, so as to keep the main body stable during magnetic resonance scanning.

(2) A container 2. A circulating liquid is provided in the container. The circulating liquid is a liquid containing hydrogen protons at any normal temperature.

The liquid containing hydrogen protons includes water, aqueous solution, liquid organic matters, etc.

(3) A tube. The tube includes a first tube 4 and a second tube 5; one end of the first tube 4 is in communication with the container 2, and the other end is in communication with a liquid inlet of the phantom main body 1; one end of the second tube 5 is in communication with the container 2, and the other end is in communication with a liquid outlet of the phantom main body 1; and the first tube 4, the phantom main body 1, the second tube 5 and the container 2 jointly form a closed loop.

The tube is a plastic hose.

The tube is used to connect the circulating liquid and the pump such that the circulating liquid circulates in the phantom main body to generate the perfusion signal. For example, the hose is an ABS plastic hose.

(4) A pump 3. The pump is provided on the first tube 4 and used to drive the circulating liquid to circulate along the closed loop to generate a perfusion signal in the phantom main body 1.

Specifically, the pump is a controllable flow pump.

The flow of the controllable flow pump can be adjusted manually or mechanically.

In this embodiment, a quality control phantom for ASL perfusion imaging equivalent to a standard brain shape is provided. The circulating liquid of the phantom is 0.1 mmol/l Gd-DTPA aqueous solution, and the tube is a hose.

Figure 4:
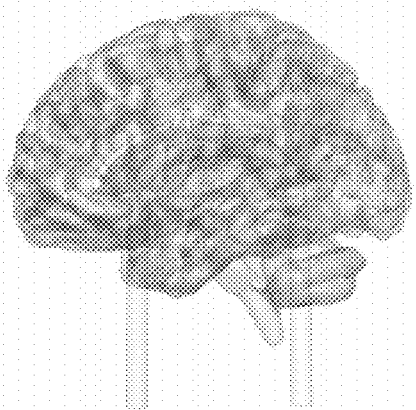
FIG. 4 illustrates a perspective view of a brain phantom main body housing and a tube provided by one embodiment of the present disclosure.

The phantom main body, as illustrated in FIG. 3, includes a cylindrical supporting member, an internal supporting member, a phantom housing, a hose, etc. The shape of the phantom housing is equivalent to the shape of an MNI standard brain, two circular holes with a diameter of 4 cm are opened in a lower portion to allow the hose to pass through, and one hole is opened at an upper portion to infuse boiling gel solution, as illustrated in FIG. 4. The phantom housing and the supporting member are made of ABS plastic by adopting a 3D printing technology. Agarose mixed gel is filled inside. The agarose concentration in the mixed gel is 1.2%, mixed with 0.75 mmol/L $CuSO_4$ and NaCl with concentration of 0.3%.

A process for preparing agarose gel includes mixing agarose powder with $CuSO_4$, NaCl and distilled water, heating the mixed solution to boiling in a microwave oven, and then performing cooling to form the gel. The hose is an ABS plastic hose with a diameter of 4 cm.

A process for making a phantom main body is as follows:

The housing with an MNI standard brain shape and a supporting member are printed by adopting 3D printing, and the hose is enabled to pass through the two circular holes in the lower portion of the phantom housing, a sealing ring is added to prevent liquid leakage, then boiling gel mixed solution is poured into the housing through the hole in the upper portion of the housing, a sealing plug is inserted, and the housing is placed upside down for cooling and solidification to obtain the phantom main body. This process may be repeated several times in a hot water bath to ensure that the hose position is fixed and there is no space inside the housing.

The quality control phantom for magnetic resonance arterial spin labeling perfusion imaging provided by this embodiment includes a phantom main body, a container, a tube and a pump, the tube includes a first tube and a second tube, and the first tube, the phantom main body, the second tube and the container jointly form a closed loop; the pump drives the circulating liquid to circulate along the closed loop to generate a perfusion signal in the phantom main body. The structure is simple, the accuracy of magnetic resonance ASL perfusion imaging can be quantitatively verified and evaluated, and it can be applied to magnetic resonance imaging systems of major manufacturers, can be applied to quantitative evaluation of pulsed, continuous or pseudo-continuous ASL perfusion imaging, can be applied to quantitative verification and evaluation of all imaging methods such as 2D ASL and 3D ASL perfusion imaging, and can also be applied to verification of ASL processing software.

This embodiment also provides a quantitative evaluation method for magnetic resonance arterial spin labeling perfusion imaging.

The quantitative evaluation method for magnetic resonance arterial spin labeling perfusion imaging provided by this embodiment includes:

In step 1, magnetic resonance arterial spin labeling sequence scanning is performed on the quality control phantom for magnetic resonance arterial spin labeling perfusion imaging as illustrated in FIG. 1 in a working state by using a magnetic resonance system.

Specifically, during MRI scanning, the main body of the ASL phantom is placed flat on an MRI scanning platform, the pump is turned on, the flow is adjusted to allow the circulating liquid to flow inside the phantom main body, transverse scanning is performed on the main body of the ASL phantom by adopting a pulsed or pseudo-continuous ASL sequence, and scanning parameters are set according to the parameters recommended in the white book of arterial spin labeling technology: Recommended implementation of arterial spin-labeled perfusion MRI for clinical applications: A consensus of the ISMRM perfusion study group and the European consortium for ASL in dementia.

In step 2, parameters of a magnetic resonance arterial spin labeling sequence are recorded, and a control image and a label image of the phantom are obtained after scanning.

After scanning, the values of relevant parameters are recorded, and the control image and the label image of the phantom are obtained.

In step 3, a cerebral blood flow is calculated through the control image and the label image.

Image analysis: a cerebral blood flow is calculated through the control image and the label image. For an image acquired by adopting a continuous or pseudo-continuous ASL sequence, the CBF of each voxel is calculated according to the following equation:

$$CBF = \frac{6000 \cdot \lambda \cdot (SI_{control} - SI_{label}) \cdot e^{\frac{PLD}{T_{1,blood}}}}{2 \cdot \alpha \cdot T_{1,blood} \cdot SI_{PD} \cdot \left(1 - e^{-\frac{\tau}{T_{1,blood}}}\right)} [\text{ml}/100 \text{ g/min}] \quad (1)$$

For an image acquired by adopting a pulsed ASL sequence, the CBF of each voxel is calculated according to the following equation:

$$CBF = \frac{6000 \cdot \lambda \cdot (SI_{control} - SI_{label}) \cdot e^{\frac{TI}{T_{1,blood}}}}{2 \cdot \alpha \cdot TI_1 \cdot SI_{PD}} [\text{ml}/100 \text{ g/min}] \quad (2)$$

In equation (1) and equation (2), $\lambda$ represents a brain tissue/blood distribution coefficient of 0.9 ml/g, $SI_{control}$ and $SI_{label}$ respectively represent time average signal intensity of control and label images, $T_{1,blood}$ represents longitudinal relaxation time of blood in unit of second, and $\alpha$ represents labeling efficiency, $\alpha=0.85$ for a continuous or pseudo-continuous ASL sequence, and $\alpha=0.98$ for a pulsed ASL sequence. $SI_{PD}$ represents signal intensity of a proton density weighted image, and $\tau$ represents labeling duration. PLD represents post-labeling delay, that is, how long to start acquiring data after labeling, and TI represents inversion time. Note that TI is an ASL sequence term of pulsed labeling, and PLD is an ASL sequence term of pseudo-continuous labeling.

$TI_1$ represents time domain width when label blood in a pulsed ASL sequence reaches a scanning field. In equation (1) and equation (2), the values of A and a are known, $SI_{control}$, $SI_{label}$ and $SI_{pd}$ need to be obtained from the acquired image, and $T_{1,blood}$, $\tau$, PLD, TI and $TI_1$ are obtained from ASL sequence information of the magnetic resonance system.

In step 4, verification is performed by comparing the calculated cerebral blood flow with an actual flow value of a controllable flow pump.

Specifically, the average percentage error $\bar{e}$ of cerebral blood flows obtained in repetitive scanning is defined as:

$$\bar{e} = \frac{1}{n} \sum_{i=1}^{n} \frac{F_i' - F_i}{F_i} \times 100\% \qquad (3)$$

In equation (3), n represents number of experiment times, $F_i'$ represents a CBF value obtained through magnetic resonance ASL scanning in an ith time of scanning, and $F_i$ represents an actual value of flow in the ith time of scanning.

A correlation coefficient p between cerebral blood flows obtained from the magnetic resonance ASL sequence and actual flows is defined as:

$$p = \frac{\sum_{i=1}^{n} (F_i' - \overline{F'}) \cdot (F_i - \overline{F})}{\sqrt{\sum_{i=1}^{n} (F_i' - \overline{F'})} \cdot \sqrt{\sum_{i=1}^{n} (F_i - \overline{F})}} \qquad (4)$$

In equation (4), n represents number of experiment times, $F_i'$ represents a CBF value obtained through magnetic resonance ASL scanning in an ith time of scanning, $\overline{F'}$ represents an average value of CBF obtained through magnetic resonance ASL scanning in n times of scanning, $F_i$ represents an actual value of flow in the ith time of scanning, F represents an average value of actual flows obtained in n times of experiments. The smaller the e is, the closer the p is to 1, indicating that the measurement accuracy of magnetic resonance ASL cerebral blood flows is higher, vice versa. The ASL sequence is quantitatively evaluated and verified by calculating the average percentage error and the correlation coefficient p.

Processing software verification: ASL data processing software commonly used includes Statistical parametric mapping (SPM12), ASLtbx, Automated Software for ASL Processing (ASAP), etc. The ASL processing software is verified by adopting the quality control phantom for magnetic resonance ASL perfusion imaging. A Montreal Neurological Institute (MNI) standard brain shape is selected as the shape of the phantom housing. The housing is made by adopting a 3D printing technology. A cylindrical supporting member is printed on an outer side of the housing to support the housing. Two circular holes are opened in the bottom of the housing to allow the hose to pass through. The filler in the housing is optional. The phantom is scanned, and then the obtained image is processed by the processing software. A processing process mainly includes steps such as CBF calculation, image denoising, partial volume effect correction, spatial standardization and skull stripping. These steps in the processing process can be implemented by adopting the existing technical solution. Then, the flow area of the hose is selected through the software to extract the CBF value. At the same time, the theoretical value of the CBF is calculated according to equation (1) or (2), and the CBF value calculated by the software and the theoretically calculated CBF value are compared with the actual flow value of the controllable flow pump for validation. The flow value may be changed to carry out repetitive experiments, and the parameters described in equation (3) and equation (4) are calculated, so as to perform quality verification and evaluation on the ASL processing software.

In this embodiment, magnetic resonance arterial spin labeling sequence scanning is performed on the quality control phantom for magnetic resonance arterial spin labeling perfusion imaging in a working state by using a magnetic resonance system, and an average percentage error of cerebral blood flows obtained in repetitive scanning and a correlation coefficient between cerebral blood flows and actual flows are calculated. The smaller the average percentage error of cerebral blood flows is, the closer the correlation coefficient between cerebral blood flows and actual flows is to 1, indicating that the measurement accuracy of magnetic resonance arterial spin labeling cerebral blood flows is higher, thus realizing the quantitative evaluation of magnetic resonance arterial spin labeling perfusion imaging.

The specific implementations of the present disclosure are described above with reference to the accompanying drawings, but are not intended to limit the protection scope of the present disclosure. A person skilled in the art should understand that various modifications or transformations may be made without creative efforts based on the technical solutions of the present disclosure, and such modifications or transformations shall fall within the protection scope of the present disclosure.

What is claimed is:

1. A quantitative evaluation method for magnetic resonance arterial spin labeling perfusion imaging, comprising:
    performing magnetic resonance arterial spin labeling sequence scanning on a quality control phantom for magnetic resonance arterial spin labeling perfusion imaging in a working state by using a magnetic resonance system, the quality control phantom for magnetic resonance arterial spin labeling perfusion imaging comprising:
        a phantom main body;
        a container, a circulating liquid being provided in the container;
        a tube, comprising a first tube and a second tube, one end of the first tube being in communication with the container, the other end being in communication with a liquid inlet of the phantom main body, one end of the second tube being in communication with the container, the other end being in communication with a liquid outlet of the phantom main body, and the first tube, the phantom main body, the second tube and the container jointly forming a closed loop; and
        a pump, provided on the first tube and used to drive the circulating liquid to circulate along the closed loop to generate a perfusion signal in the phantom main body;
    recording parameters of a magnetic resonance arterial spin labeling sequence, and obtaining a control image and a label image of the phantom after scanning;
    calculating a cerebral blood flow through the control image and the label image;
    performing verification by comparing the calculated cerebral blood flow with an actual flow value of a controllable flow pump.

2. The quantitative evaluation method for magnetic resonance arterial spin labeling perfusion imaging according to claim 1, wherein the method also comprises: adjusting the flow of the pump and performing repetitive scanning experiments.

3. The quantitative evaluation method for magnetic resonance arterial spin labeling perfusion imaging according to claim 1, wherein the method also comprises: calculating an average percentage error of cerebral blood flows obtained in repetitive scanning and a correlation coefficient between cerebral blood flows and actual flows.

4. The quantitative evaluation method for magnetic resonance arterial spin labeling perfusion imaging according to claim 3, wherein the smaller the average percentage error of cerebral blood flows is, the closer the correlation coefficient between cerebral blood flows and actual flows is to 1, indicating that the measurement accuracy of magnetic resonance arterial spin labeling cerebral blood flows is higher.

* * * * *